(12) United States Patent
Hong et al.

(10) Patent No.: US 12,303,805 B2
(45) Date of Patent: May 20, 2025

(54) CONTINUOUS POST-TREATMENT METHOD AND DEVICE FOR PENEM COMPOUND

(71) Applicant: ASYMCHEM LABORATORIES (TIANJIN) CO., LTD., Tianjin (CN)

(72) Inventors: Hao Hong, Morrisville, NC (US); Liang Hong, Tianjin (CN); Jian Tao, Tianjin (CN); Jinhai Guo, Tianjin (CN); Xian Cheng, Tianjin (CN); Yan Zhang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 313 days.

(21) Appl. No.: 17/769,200

(22) PCT Filed: Oct. 15, 2019

(86) PCT No.: PCT/CN2019/111198
§ 371 (c)(1),
(2) Date: Apr. 14, 2022

(87) PCT Pub. No.: WO2021/072622
PCT Pub. Date: Apr. 22, 2021

(65) Prior Publication Data
US 2024/0115972 A1    Apr. 11, 2024

(51) Int. Cl.
*C07D 477/02* (2006.01)
*B01D 9/00* (2006.01)
*B01D 11/04* (2006.01)

(52) U.S. Cl.
CPC ........ *B01D 11/0446* (2013.01); *B01D 9/0054* (2013.01); *B01D 11/0484* (2013.01); *B01D 11/0488* (2013.01); *B01D 11/0492* (2013.01); *C07D 477/02* (2013.01); *B01D 2009/0086* (2013.01)

(58) Field of Classification Search
CPC .................... C07D 477/00; C07D 477/02; B01D 11/0445; B01D 9/0054; B01D 11/0492
See application file for complete search history.

(56) References Cited

FOREIGN PATENT DOCUMENTS

| | | |
|---|---|---|
| CN | 102250145 A | 11/2011 |
| CN | 102260264 A | 11/2011 |
| CN | 102633801 A | 8/2012 |
| CN | 108837558 A | 11/2018 |
| CN | 109776646 A | 5/2019 |
| JP | 2012525339 A | 10/2012 |
| WO | 2007111328 A1 | 10/2007 |

OTHER PUBLICATIONS

International Search Report issued in connection with PCT Application No. PCT/CN2019/111198 dated Jul. 15, 2020.

*Primary Examiner* — Sikarl A Witherspoon
(74) *Attorney, Agent, or Firm* — Dennemeyer & Associates LLC

(57) ABSTRACT

Provided are a continuous post-treatment method and device for a penem compound. The method includes the following steps: S1, performing continuous extraction on a reaction crude product of a penem compound, to obtain an extraction heavy phase and an extraction light phase; S2, performing continuous solid-liquid separation on the extraction heavy phase, to obtain a liquid phase separation product; S3, performing continuous pH adjustment on the liquid phase separation product until a pH value thereof is 6.1-6.3, to obtain pH-adjusted solution; and S4, performing continuous crystallization treatment on the pH-adjusted solution by a first crystallization solvent, to obtain a penem compound product. The use of the method has the advantages of high treatment speed and high efficiency, and stable material properties and a low deterioration rate during the treatment, and has better control over the yield and purity of a target product.

20 Claims, 1 Drawing Sheet

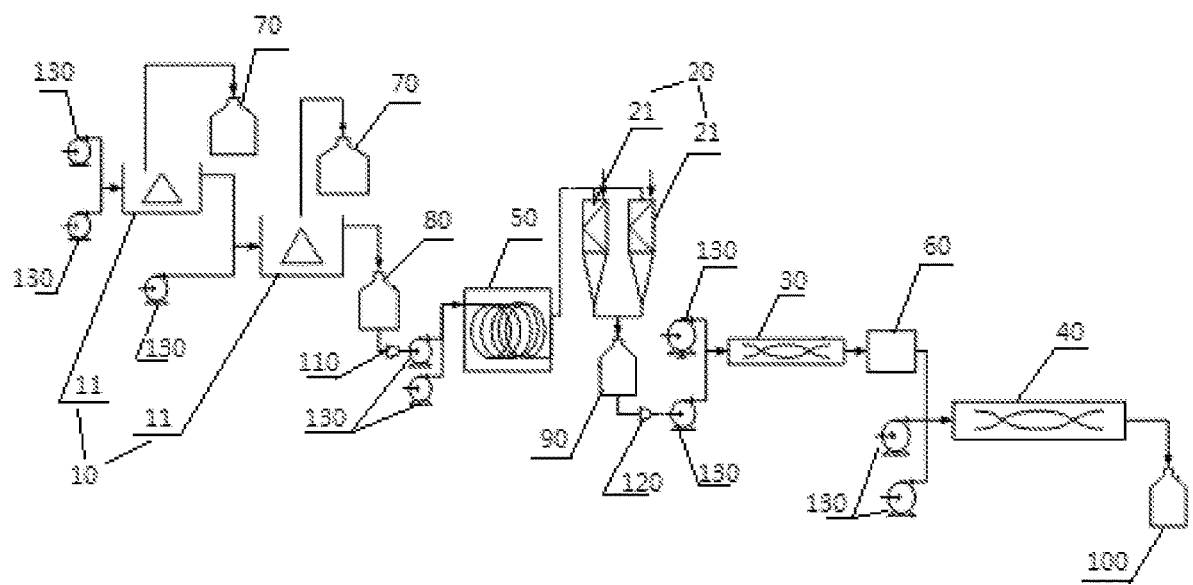

CONTINUOUS POST-TREATMENT METHOD AND DEVICE FOR PENEM COMPOUND

TECHNICAL FIELD

The disclosure relates to the technical field of organic synthesis, in particular to a continuous post-treatment method and device for a penem compound.

BACKGROUND

In the existing pharmaceutical and chemical industry fields, the post-treatment of a reaction system is one of researches that may never be avoided. Usually, a unit operation of the post-treatment mainly includes: extraction and liquid separation, press-filtering, drying, pH adjustment, crystallization, and centrifugation. Existing domestic chemical and pharmaceutical industries are mainly based on batch post-treatment, namely a batch-type operation of a single post-treatment operating unit, and the advantage is that the amount of single-batch treatment is large. The disadvantages are time-consuming, labor-consuming and a low degree of automation. If a post-treatment system is deteriorated over time, the batch post-treatment may lose a lot of products. Commonly used penem antibiotics belong to this perishable type (for example, these problems exist in a post-treatment method provided in a patent CN207845524U).

Specifically, in an existing industry, a post-treatment technology for a penem large-batch reaction system is relatively simple. In terms of extraction and liquid separation, a large kettle is commonly used in workshop production for batch treatment and liquid separation. The consume time of the single operating unit is 6 hours. In an aqueous phase containing a product after extraction and separation, a solvent residue (1-ethyl-2-pyrrolidinone (NEP), 1,1,3,3-tetramethylguanidine (TMG), and isoamyl alcohol) is larger. The residual product dissolved in the organic phase may reach 0.3%, and secondary extraction and liquid separation operations are often performed. It may be said that the traditional batch extraction and liquid separation operation is time-consuming and labor-consuming, and the separation effect is not very good. Moreover, in a pH adjustment stage of a penem post-treatment flow, the disadvantage of the batch adjustment of pH is that an acetic acid is repeatedly added and then stirred and stood, this may cause the longer time-consuming. The time of the pH adjustment stage in a single batch of a 400 L batch treatment volume may reach 5-6 hours, and once the adjustment is finished, the loss is very large. This also means that the deterioration rate of the penem product is increased during the pH adjustment period (usually, the deterioration rate of the product per hour is about 0.2% before the pH adjustment stage, and the deterioration rate of the product per hour is about 1.3% after the acid adjustment. In the existing industry, the post-treatments for an ertapenem are all a batch process, the treatment time is long so that the product deterioration rate is high, and the yield is lower), the loss is increased, the product yield and the product purity may be greatly affected, this is the results caused by limitations of a treatment mode itself. In addition, the large-batch treatment reaction system brings many hidden dangers. For example, heat release, gas discharge, and material leakage, such as a penem product may have different degrees of the heat release in a mixing and press-filtering section and a crystallization section. The batch treatment volume is larger, the potential dangers brought are also very much. If properties of a treated material are relatively poor, the maintenance cost may be greatly increased. The batch post-treatment is large in occupied area, and very high in human resource and energy consumption costs.

In view of this situation, it is urgent to develop a post-treatment technology with a fast post-treatment speed, high treatment efficiency and stable material properties.

SUMMARY

A main purpose of the present disclosure is to provide a continuous post-treatment method and device for a penem compound, as to solve problems in an existing technology that in the process of batch treatment of a penem compound crude product, the treatment speed is low, the efficiency is low and the material deterioration rate is high.

In order to achieve the above purpose, according to one aspect of the present disclosure, a continuous post-treatment method for a penem compound is provided, it includes the following steps: S1, performing continuous extraction on a reaction crude product of a penem compound, to obtain an extraction heavy phase and an extraction light phase; S2, performing continuous solid-liquid separation on the extraction heavy phase, to obtain a liquid phase separation product; S3, performing continuous pH adjustment on the liquid phase separation product until a pH value thereof is 6.1-6.3, to obtain pH-adjusted solution; and S4, performing continuous crystallization treatment on the pH-adjusted solution by using a first crystallization solvent, to obtain a penem compound product.

Further, before performing the continuous solid-liquid separation on the extraction heavy phase, the step S2 further includes a step of adding a second crystallization solvent to the extraction heavy phase and mixing the two in a plug flow reactor (PFR); and the added amount of the second crystallization solvent is 50~80% of the weight of the extraction heavy phase, and the temperature of the PFR is controlled to −7~3° C.

Further, the retention time of the extraction heavy phase in the PFR is 2~8 min.

Further, in the step S1, the continuous extraction process includes N times in sequence, N≥2, and the heavy phase separated in the M-th time of the continuous extraction process enters the M+1-th time of the continuous extraction process, 1≤M≤(N−1), the heavy phase separated in the N-th time of the continuous extraction process is used as the extraction heavy phase in the step S2; and preferably, N=2.

Further, in the continuous extraction process, the retention time of the reaction crude product of the penem compound is 1~7 min, and the treatment temperature is −7~3° C.

Further, in the process of the continuous solid-liquid separation, the extraction heavy phase is divided into a plurality of parts, and the plurality of the parts of the extraction heavy phases respectively enter different press-filtering devices for treatment each to each, and the treatment flux of each press-filtering device is 1~2 L/min, the retention time of the extraction heavy phase is 2~11 min.

Further, the first crystallization solvent is selected from one or more of a group consisting of methanol and n-propanol, and the second crystallization solvent is selected from one or more of a group consisting of methanol and n-propanol.

Further, in the continuous crystallization treatment process, the retention time of the pH-adjusted solution is 2~11 min, and the treatment temperature is −22~12° C.

Further, in the step S3, a reagent for adjusting a pH value of a liquid phase separator is a mixed solution of methanol and acetic acid, and preferably the pH value thereof is 3~4.

Further, in the process of adjusting the pH value of the liquid phase separator, the retention time of the liquid phase separator is 2~11 min, and the treatment temperature is −7~3° C.

According to another aspect of the present disclosure, a continuous post-treatment device for a penem compound is provided, it includes: a continuous extraction and liquid separation unit, provided with a penem compound crude product inlet, an extractant inlet, an extraction heavy phase outlet and an extraction light phase outlet, herein the continuous extraction and liquid separation unit is used for continuous extraction of a reaction crude product of the penem compound; a continuous press-filtering unit, provided with a press-filtering inlet, a solid phase outlet and a liquid phase outlet, herein the press-filtering inlet is connected with the extraction heavy phase outlet, and the continuous press-filtering unit is used for continuous solid-liquid separation of the extraction heavy phase discharged from the extraction heavy phase outlet; a continuous pH adjustment unit, provided with a liquid phase inlet, a pH adjuster inlet and an adjusting liquid outlet, herein the liquid phase inlet is connected with the liquid phase outlet, and the continuous pH adjustment unit is used for continuous pH adjustment of the liquid discharged from the liquid phase outlet; and a continuous crystallization unit, provided with an adjusting liquid inlet, a first crystallization solvent inlet and a crystallization slurry outlet, herein the adjusting liquid inlet is connected with the adjusting liquid outlet, and the continuous crystallization unit is used for continuous crystallization of the pH-adjusted solution discharged from the adjusting liquid outlet.

Further, the device further includes a PFR, arranged on a pipeline connected with the press-filtering liquid inlet and the extraction heavy phase outlet, and the PFR is further provided with a second crystallization solvent inlet.

Further, the PFR is a jacketed coil reactor, and it includes a coil reactor and a first temperature control jacket arranged outside the coil reactor.

Further, the continuous pH adjustment unit is a tube-type pH adjustment device, and the continuous crystallization unit is a tube-type crystallization device.

Further, the device further includes: a pH value detection device, arranged on a pipeline connected with the adjusting liquid inlet and the adjusting liquid outlet, and used to detect a pH value of the pH-adjusted solution.

Further, the continuous extraction and liquid separation unit includes multi-level of continuous extraction and liquid separation devices arranged serially in sequence, and each continuous extraction and liquid separation device is provided with a liquid inlet, an extractant inlet, an extraction light phase outlet and an extraction heavy phase outlet, and the liquid inlet of the continuous extraction and liquid separation device located at the most upstream is the penem compound crude product inlet, and the extraction heavy phase outlet of the continuous extraction and liquid separation device located at the most downstream is connected with the press-filtering liquid inlet, and in two adjacent continuous extraction and liquid separation devices, the extraction heavy phase outlet located in the upstream level is connected with the liquid inlet located in the downstream level.

Further, the continuous press-filtering unit includes multi-level press-filtering devices arranged in parallel, and each multi-level press-filtering device is provided with a press-filtering inlet, a solid phase outlet and a liquid phase outlet.

Further, the device further includes: an extraction light phase receiving device, connected with the extraction light phase outlet; an extraction heavy phase receiving device, arranged on a pipeline connected with the extraction heavy phase outlet and the PFR; a liquid phase receiving device, arranged on a pipeline connected with the liquid phase inlet and the liquid phase outlet; and a crystallization slurry receiving device, connected with the crystallization slurry outlet.

Further, the device further includes: a first mass flow meter, arranged on a pipeline connected with the extraction heavy phase receiving device and the PFR; and a second mass flow meter, arranged on a pipeline connected with the liquid phase receiving device and the liquid phase inlet; and the device further includes a control unit, herein the control unit is electrically connected with the pH value detection device, the first mass flow meter and the second mass flow meter.

Further, the pipelines on which the penem compound crude product inlet, the extractant inlet, the pH adjuster inlet, the liquid phase inlet, the first crystallization solvent inlet, the adjusting liquid inlet, the second crystallization solvent inlet and the inlet of the PFR for feeding the extraction heavy phase are located are all provided with a material delivery pump.

Further, the continuous extraction and liquid separation unit, the continuous press-filtering unit, the continuous pH adjustment unit and the continuous crystallization unit are all provided with a temperature control unit, and the extraction heavy phase receiving device is provided with a second temperature control jacket, the liquid phase receiving device is provided with a third temperature control jacket, the crystallization slurry receiving device is provided with a fourth temperature control jacket, and the control unit is also electrically connected with the temperature control unit, the second temperature control jacket, the third temperature control jacket and the fourth temperature control jacket.

Further, the continuous post-treatment device for the penem compound is a post-treatment device for penem compound synthesis.

The present disclosure provides a continuous post-treatment method for a penem compound, and it is a continuous integrated post-treatment method. This method has the advantages of a fast treatment speed and high efficiency while the method is used for the post-treatment of the reaction crude product of the penem compound, and in the treatment process, the properties of the material are stable, the deterioration rate is low, and it has the better control ability to the yield and purity of the target product. In particular, this method may fit well with the properties of the penem compound, and has the stronger pertinence in reducing the product deterioration rate, and improving the treatment effects and product yield.

BRIEF DESCRIPTION OF THE DRAWINGS

Drawings of the description for constituting a part of the present application are used to provide further understanding of the present disclosure. Exemplary embodiments of the present disclosure and descriptions thereof are used to explain the present disclosure, and do not constitute improper limitation to the present disclosure. In the drawings:

FIG. 1 shows a structure schematic diagram of a continuous post-treatment device for a penem compound according to an embodiment of the present disclosure.

Herein, the above drawings include the following reference signs:

10. Continuous extraction and liquid separation unit; 11. Continuous extraction and liquid separation device; 20. Continuous press-filtering unit; 21. Press-filtering device; 30. Continuous pH adjustment unit; 40. Continuous crystallization unit; 50. Plug flow reactor; 60. PH value detection device; 70. Extraction light phase receiving device; 80. Extraction heavy phase receiving device; 90. Liquid phase receiving device; 100. Crystallization slurry receiving device; 110. First mass flow meter; 120. Second mass flow meter; and 130. Material delivery pump.

DETAILED DESCRIPTION OF THE EMBODIMENTS

It should be noted that embodiments in the present application and features in the embodiments may be combined with each other in the case without conflicting. The present disclosure is described in detail below with reference to the drawings and in combination with the embodiments.

As described in the background, while batch treatment of a penem compound crude product is used in an existing technology, there are problems such as a low treatment speed, low efficiency, and a high material deterioration rate.

In order to solve this problem, the present disclosure provides a continuous post-treatment method for a penem compound, and it includes the following steps: S1, performing continuous extraction on a reaction crude product of a penem compound, to obtain an extraction heavy phase and an extraction light phase; S2, performing continuous solid-liquid separation on the extraction heavy phase, to obtain a liquid phase separation product; S3, performing continuous pH adjustment on the liquid phase separation product until a pH value thereof is 6.1~6.3, to obtain pH-adjusted solution; and S4, performing continuous crystallization treatment on the pH-adjusted solution by using a first crystallization solvent, to obtain a penem compound product.

The present disclosure provides a continuous integrated post-treatment method for a penem compound. This method has the advantages of a fast treatment speed and high efficiency while the method is used for the post-treatment of the reaction crude product of the penem compound, and in the treatment process, the properties of the material are stable, the deterioration rate is low, and it has the better control ability to the yield and purity of the target product. In particular, this method may fit well with the properties of the penem compound, and has the stronger pertinence in reducing the product deterioration rate, and improving the treatment effects and product yield.

Specifically, in the extraction and liquid separation stage, the continuous extraction and liquid separation used in the present disclosure shortens the time by more than 50% compared to the intermittent-type batch post-treatment, and the treatment effect is far better than the batch treatment. In the press-filtering stage, the heat release per unit time is much lower than the batch post-treatment, this means that more energy is saved and the stability of the product is guaranteed. The system which is treated already in the pH adjustment stage immediately enters the crystallization stage, and the retention time is greatly shortened, this means that the product deterioration rate is greatly reduced. In the crystallization stage, the continuous treatment not only overcomes a problem of the batch post-treatment that the efficiency is low. At the same time, the crystallization system has the better advantage than the batch treatment system in the later stage of crystal shape screening.

In a preferred embodiment, before performing the continuous solid-liquid separation on the extraction heavy phase, the step S2 further includes a step of adding a second crystallization solvent to the extraction heavy phase and mixing the two in a plug flow reactor (PFR); and the added amount of the second crystallization solvent is 50~80% of the weight of the extraction heavy phase, and the temperature of the PFR is controlled to −7~3° C. In this way, before the extraction heavy phase enters the press-filtering stage, it is pre-mixed with a part of the crystallization solvent. On the one hand, it is beneficial to the growth of a solid phase of the catalyst in the crude product system, thereby it is beneficial to the solid-liquid separation in the press-filtering stage, and on the other hand, the addition of a small amount of the crystallization solvent is also beneficial to the stability of the product in a solution system (a small amount of the crystallization solvent may not cause the product to be separated out, and a large amount of the crystallization solution in the crystallization stage may cause the product to be crystallized out due to a solubility problem), and plays a role of buffering and stabilizing the liquid phase system of the product, thereby it is beneficial to prevent the blockage of the subsequent pH adjustment process, so that the continuous treatment process is more stable.

In the actual operation process, because the PFR is used for mixing, the extraction heavy phase is a continuous flow process in the PFR, it is mixed with the second crystallization solvent while flowing, and the retention time is short. In order to further improve the mixing effect, in a preferred embodiment, the retention time of the extraction heavy phase in the PFR is 2~8 min.

In a preferred embodiment, in the step S1, the continuous extraction process includes N times in sequence, N≥2, and the heavy phase separated in the M-th time of the continuous extraction process enters the M+1-th time of the continuous extraction process, 1≤M≤(N−1), the heavy phase separated in the N-th time of the continuous extraction process is used as the extraction heavy phase in the step S2; and preferably, N=2. In this way, after the first time of the continuous extraction and separation of the penem compound reaction crude product to be treated, two phases are continuously separated, the light phase may be recovered by the solvent, and the heavy phase enters the next continuous extraction process. In the actual treatment process, the specific treatment times may be selected according to the treatment volume and product concentration of the crude product, and the separation levels may also be determined according to the difficulty of extraction and separation. The treatment time and the separation effect of the treatment volume are more effective than a batch process. More preferably, in the continuous extraction process, the retention time of the reaction crude product of the penem compound is 1~7 min, and the treatment temperature is −7~3° C.

In a preferred embodiment, in the process of the continuous solid-liquid separation, the extraction heavy phase is divided into a plurality of parts, and the plurality of the parts of the extraction heavy phases respectively enter different press-filtering devices for treatment each to each, and the treatment flux of each press-filtering device is 1~2 L/min, the retention time of the extraction heavy phase is 2~11 min. Because the press-filtering process is a high-pressure treatment process, the use of multi-level of press-filtering devices to treat press-filtering liquid is more beneficial to alleviate the treatment conditions of each press-filtering device.

In a preferred embodiment, the first crystallization solvent is methanol and/or n-propanol, and the second crystallization solvent is methanol and/or n-propanol. More preferably, in the continuous crystallization treatment process, the retention time of the pH-adjusted solution is 2~11 min, and the treatment temperature is −22~12° C.

In order to further improve the efficiency of pH adjustment and prevent precipitation during the pH adjustment process, in a preferred embodiment, in the above step S3, a reagent for adjusting a pH value of a liquid phase separator is mixed solution of methanol and acetic acid, and preferably the pH value thereof is 3~4. More preferably, in the process of adjusting the pH value of the liquid phase separator, the retention time of the liquid phase separator is 2~11 min, and the treatment temperature is −7~3° C.

According to another aspect of the present disclosure, a continuous post-treatment device for a penem compound is further provided, as shown in FIG. 1, the device includes a continuous extraction and liquid separation unit 10, a continuous press-filtering unit 20, a continuous pH adjustment unit 30, and a continuous crystallization unit 40, the continuous extraction and liquid separation unit 10 is provided with a penem compound crude product inlet, an extractant inlet, an extraction heavy phase outlet and an extraction light phase outlet, and the continuous extraction and liquid separation unit 10 is used for continuous extraction of a reaction crude product of the penem compound; the continuous press-filtering unit 20 is provided with a press-filtering inlet, a solid phase outlet and a liquid phase outlet, the press-filtering inlet is connected with the extraction heavy phase outlet, and the continuous press-filtering unit 20 is used for continuous solid-liquid separation of the extraction heavy phase discharged from the extraction heavy phase outlet; the continuous pH adjustment unit 30 is provided with a liquid phase inlet, a pH adjuster inlet and an adjusting liquid outlet, the liquid phase inlet is connected with the liquid phase outlet, and the continuous pH adjustment unit 30 is used for continuous pH adjustment of the liquid discharged from the liquid phase outlet; and the continuous crystallization unit 40 is provided with an adjusting liquid inlet, a first crystallization solvent inlet and a crystallization slurry outlet, the adjusting liquid inlet is connected with the adjusting liquid outlet, and the continuous crystallization unit 40 is used for continuous crystallization of the pH-adjusted solution discharged from the adjusting liquid outlet.

The above continuous post-treatment device for the penem compound is a continuous integrated post-treatment device. The device has the advantages of a fast treatment speed and high efficiency while it is used for the post-treatment of the reaction crude product of the penem compound, and in the treatment process, the properties of the material are stable, the deterioration rate is low, and it has the better control ability to the yield and purity of the target product. In particular, this device may fit well with the properties of the penem compound, and has the stronger pertinence in reducing the product deterioration rate, and improving the treatment effects and product yield.

Specifically, for the post-treatment process of a penem product, in the extraction and liquid separation stage, the continuous extraction and liquid separation used in the present disclosure shortens the time by more than 50% compared to the intermittent-type batch post-treatment, and the treatment effect is far better than the batch treatment. In the press-filtering stage, the heat release per unit time is much lower than the batch post-treatment, this means that more energy is saved and the stability of the product is guaranteed. The system which is treated already in the pH adjustment stage immediately enters the crystallization stage, and the retention time is greatly shortened, this means that the product deterioration rate is greatly reduced. In the crystallization stage, the continuous treatment not only overcomes a problem of the batch post-treatment that the efficiency is low. At the same time, the crystallization system has the better advantage than the batch treatment system in the later stage of crystal shape screening.

In a preferred embodiment, as shown in FIG. 1, the above device further includes: a plug flow reactor 50 (PFR), arranged on a pipeline connected with the press-filtering liquid inlet and the extraction heavy phase output, and the plug flow reactor 50 is further provided with a second crystallization solvent inlet. In this way, before the extraction heavy phase enters the press-filtering stage, it is pre-mixed with a part of the crystallization solvent. On the one hand, it is beneficial to the growth of a solid phase of the catalyst in the crude product system, thereby it is beneficial to the solid-liquid separation in the press-filtering stage, and on the other hand, the addition of a small amount of the crystallization solvent is also beneficial to the stability of the product in a solution system (a small amount of the crystallization solvent may not cause the product to be separated out, and a large amount of the crystallization solution in the crystallization stage may cause the product to be crystallized out due to a solubility problem), and plays a role of buffering and stabilizing the liquid phase system of the product, thereby it is beneficial to prevent the blockage of the subsequent pH adjustment process, so that the continuous treatment process is more stable.

In a preferred embodiment, the plug flow reactor 50 is a jacketed coil reactor, and it includes a coil reactor and a first temperature control jacket arranged outside the coil reactor. The use of the temperature control jacketed coil reactor is more beneficial to the mixing of the extraction heavy phase and a small amount of the crystallization solvent, so that the catalyst may be more fully separated out, and the temperature control may further guarantee the stability of the system and prevent the deterioration. At the same time, the use of the jacketed coil reactor is also beneficial to avoid a risk that the local heat release is large so as to damage the product.

In order to further improve the continuity of the treatment process, in a preferred embodiment, the continuous pH adjustment unit 30 is a tube-type pH adjustment device, and the continuous crystallization unit 40 is a tube-type crystallization device. The tube-type device is used, as the advance of the material in the tube-type device, the material mixing is more uniform, and it has more advantages in terms of treatment efficiency and effect. More preferably, the continuous pH adjustment unit 30 is a flat plug flow type or a fully mixed flow type, and the continuous crystallization unit 40 is a flat plug flow type.

In a preferred embodiment, the above device further includes: a pH value detection device 60, arranged on a pipeline connected with the adjusting liquid inlet and the adjusting liquid outlet, and used for detecting a pH value of the pH adjusting liquid. The present disclosure adopts a pH pre-feedback adjustment form, and by monitoring the pH value state of the adjusting liquid in real time, it is convenient to adjust the relative added amount of the pH adjuster in time (it may be adjusted by adjusting the added amount of the pH adjuster and/or the added amount of a product phase).

In a preferred embodiment, the continuous extraction and liquid separation unit 10 includes multi-level of continuous extraction and liquid separation devices 11 arranged serially in sequence, and each continuous extraction and liquid separation device 11 is provided with a liquid inlet, an extractant inlet, an extraction light phase outlet and an extraction heavy phase outlet, and the liquid inlet of the continuous extraction and liquid separation device 11 located at the most upstream is the penem compound crude product inlet, and the extraction heavy phase outlet of the continuous extraction and liquid separation device 11 located at the most downstream is connected with the press-filtering liquid inlet, and in two adjacent continuous extraction and liquid separation devices 11, the extraction heavy phase outlet located in the upstream level is connected with the liquid inlet located in the downstream level. In this way, after the penem compound reaction crude product to be treated is extracted and separated in the first-level of the continuous extraction and liquid separation device 11, the two phases are continuously separated, the light phase may be recovered by the solvent, and the heavy phase enters the next level of the continuous extraction and liquid separation device 11 for further extraction and separation. In the actual treatment process, the level number of the specific continuous extraction and liquid separation device 11 may be selected according to the treatment volume and product concentration of the crude product, and the separation level number may also be determined according to the difficulty of extraction and separation, so it has the great advantage in the treatment time and the separation effect of the treatment volume compared to the batch process.

Similarly, the scale of the continuous press-filtering unit 20 may be selected according to the size of the treatment volume. In a preferred embodiment, the continuous press-filtering unit 20 includes multi-level press-filtering devices 21 arranged in parallel, and each multi-level press-filtering device 21 is provided with a press-filtering inlet, a solid phase outlet and a liquid phase outlet. Because the press-filtering process is a high pressure treatment process, the use of the multi-level press-filtering devices 21 arranged in parallel to treat the press-filtering liquid is more beneficial to alleviate the treatment conditions of each press-filtering device.

In a preferred embodiment, the above device further includes: an extraction light phase receiving device 70, connected with the extraction light phase outlet; an extraction heavy phase receiving device 80, arranged on a pipeline connected with the extraction heavy phase outlet and the plug flow reactor 50; a liquid phase receiving device 90, arranged on a pipeline connected with the liquid phase inlet and the liquid phase outlet; and a crystallization slurry receiving device 100, connected with the crystallization slurry outlet. By using each receiving device, a buffering device may be provided for the feeding of each stage, so that it is convenient for the adjustment of the feed flow of each stage. More preferably, the above device further includes: a first mass flow meter 110, arranged on a pipeline connected with the extraction heavy phase receiving device 80 and the plug flow reactor 50; and a second mass flow meter 120, arranged on a pipeline connected with the liquid phase receiving device 90 and the liquid phase inlet; and the device further includes a control unit, herein the control unit is electrically connected with the pH value detection device 60, the first mass flow meter 110 and the second mass flow meter 120. In this way, the feeding conditions of each stage may be more conveniently adjusted by the control unit, and at the same time, the operating conditions of each stage may be also monitored in real time, so that the treatment process is more stable, thereby the probability of product deterioration is further reduced, and the treatment efficiency is improved.

In a preferred embodiment, as shown in FIG. 1, the pipelines on which the penem compound crude product inlet, the extractant inlet, the pH adjuster inlet, the liquid phase inlet, the first crystallization solvent inlet, the adjusting liquid inlet, the second crystallization solvent inlet and the inlet of the plug flow reactor 50 for feeding the extraction heavy phase are located are all provided with a material delivery pump 130. It should be noted that in the crystallization stage, as the adjusting liquid and a large amount of the crystallization solvent are mixed in the tube-type crystallization device, the target product is forced to crystallize out, and the crystallization slurry is a solid-liquid two-phase mixed system. The material delivery pump 130 is used for material-driven delivery, so that the adjusting liquid and the crystallization solvent may achieve very good mixing and turbulence, and the crystallization effect and efficiency thereof are better than batch treatment modes. More preferably, the above continuous crystallization unit 40 is a tube-type flat plug flow crystallization device, and this is more beneficial to improve the crystallizing effect. In addition, the retention time of single system particles in the device is extremely short after the pH adjustment is completed, this is more beneficial to improve the crystallization effect.

In the actual operation process, before the adjusting liquid enters, the material delivery pump 130 may be used to continuously quantify the feeding in advance so as to fill the tube-type crystallization device with the crystallization solvent, and then the adjusting liquid is fed through the material delivery pump 130 for the crystallization treatment. The material delivery pump 130, through a large-flow and high-pressure-resistant oscillating device, continuously delivers energy to the tube-type crystallization device, so that the solid-liquid mixed slurry after the crystallization may not be blocked in the tube-type crystallization device, and a slurry-like system enters the crystallization slurry receiving device 100 for temporary storage at a low temperature. At this time, the system is very stable and is not deteriorated over time. After standing for a period of time, it enters the solid-liquid separation device to obtain a qualified product.

In a preferred embodiment, the continuous extraction and liquid separation unit 10, the continuous press-filtering unit 20, the continuous pH adjustment unit 30 and the continuous crystallization unit 40 are all provided with a temperature control unit, and the extraction heavy phase receiving device 80 is provided with a second temperature control jacket, the liquid phase receiving device 90 is provided with a third temperature control jacket, the crystallization slurry receiving device 100 is provided with a fourth temperature control jacket, and the control unit is also electrically connected with the temperature control unit, the second temperature control jacket, the third temperature control jacket and the fourth temperature control jacket. In this way, the temperature may be controlled more accurately for each stage, thereby the stability of each stage of the post-treatment is further improved. More preferably, the above continuous extraction and liquid separation unit 10, continuous press-filtering unit 20, continuous pH adjustment unit 30, continuous crystallization unit 40, first temperature control jacket, second temperature control jacket, third temperature control jacket, and fourth temperature control jacket are all provided with a temperature-resistant platinum resistance, it is used to feed back a measured temperature to the control unit, and the above device further includes an alarm unit, and the control unit is electrically connected with the alarm unit. In this way, the measured temperature may be fed back to the control unit in time through the temperature platinum resistance, and the standard range may be set for each temperature platinum resistance. If the standard range is exceeded and the abnormal range is maintained for more than 10 s, an alarm may be given and linked with tripping. This is more beneficial to maintain the stability of each stage of the post-treatment, and adjust the temperature state of each stage in time.

The penem products are all more sensitive to the temperature. The temperature is higher, and the deterioration rate of the product is faster. Therefore, the entire continuous post-treatment device has strict temperature control measures. All product-containing receiving devices are provided with the temperature control jackets, and all operating unit devices are also provided with the temperature control jackets. The important delivery pipelines, such as a delivery section of the adjusting liquid after the pH adjustment, are also provided with the temperature control jackets and temperature-insulated.

In a preferred embodiment, the above device further includes a pressure detection unit for detecting the pressure inside the continuous press-filtering unit 20, the continuous pH adjustment unit 30, the continuous crystallization unit 40, the plug flow reactor 50, and each receiving device, and the pressure detection unit is electrically connected with the control unit. In this way, the operating pressure of each stage may be detected in real time, and it may feed back whether there is blockage in each pressure unit in time, and maintain the stable operation of the system. A pressure detection point of the pressure detection unit may be set at the inlet of the above device. More preferably, the above continuous press-filtering unit 20, continuous pH adjustment unit 30, continuous crystallization unit 40, and plug flow reactor 50 are all provided with a tail gas discharge pipeline. This may prevent pressure holding and avoid the accumulation of a tail gas at the same time.

More preferably, the above device further includes a pressure alarm system, it is electrically connected with the pressure detection unit. In this way, all the pressure measurement points of the continuous post-treatment device may be set to the standard pressure range, and once a situation of the overpressure or negative pressure occurs, the alarm may be immediately given and linked with the tripping.

The materials of the above devices, units, pipelines and the like may be designed according to the properties of the materials to be treated. For example, the materials with chemical properties, temperature and pressure resistance such as titanium, Polytetrafluoroethylene, 304 stainless steel, 316 stainless steel, and Hastelloy may be used. A connection mode between the pipelines and the devices in the whole flow is mainly a flange type, and a variety of other connection modes include: coexistent modes such as welding, quick coupling, and ferrule connector.

Preferably, the serial form of the continuous extraction and liquid separation device 11 is an overflow type, namely the extraction heavy phase in the previous level enters the next level for further extraction the overflow form. The specific type of the continuous extraction and liquid separation device 11 is preferably a centrifugal extractor, certainly, a rotating disk extraction tower or a membrane separation extraction device and the like may also be used.

Preferably, a membrane pile or a filler is used inside the above press-filtering device 21.

The above post-treatment device provided by the present disclosure is more suitable for the post-treatment of products with poor product properties and perishable quality. In a preferred embodiment, the above post-treatment device for the penem compound is a post-treatment device for synthesis of a penem compound. The specific penem compound includes but is not limited to ertapenem, imipenem, meropenem, biapenem, panipenem and the like. The present disclosure is successfully applied to the production of these penem crude products from small-scale to pilot-scale continuous post-treatment.

In addition, the above device provided by the present disclosure is a highly automated treatment device, and the feeding speed, the temperature and the like may be adjusted at any time according to the treatment volume of the device, and the overall treatment time may be accurately controlled. Each single operation unit is connected into a whole through an automated control program, and each unit operation is accurately connected through a feedback mass flow meter, so that the original intermittent operation flow achieves the continuous treatment. According to the different treatment systems, the operation unit may be increased or decreased. In terms of the safety, through installing devices of pressure, temperature, dangerous gas alarm and the like, it is adjusted with the linkage setting of overpressure, overtemperature, and excessive dangerous gas alarm at the same time, a potential risk of an accident is greatly reduced. In the case facing to an emergency situation, all feeding ports may be cut off to control the product loss and risk level within a minimum range. The present disclosure may also greatly reduce the area occupied by the device, the labor resources, and the production energy consumption. Compared with the traditional batch post-treatment technology, the investment cost is greatly reduced.

The present application is further described in detail below in combination with the specific embodiments, and it should not be construed as limiting a scope of protection claimed by the present application.

Embodiment 1

Small-scale test: a 4 L ertapenem crude product system is post-treated with the device shown in FIG. 1, and the ertapenem crude product system includes ertapenem, tetramethylguanidine (TMG), N-ethylpyrrolidone (NEP), isoamyl alcohol, a palladium-carbon catalyst, and water.

In a continuous extraction and liquid separation stage, the ertapenem crude product system is subjected to secondary extraction and liquid separation, the system is automatically continuously quantified and fed, and a first-level extractant (mixed solution of the isoamyl alcohol, water, and $NaHCO_3$ diphenyl phosphate) is automatically continuously quantified and fed at the same time. In a first-level centrifugal extractor, the first-level automatic extraction and liquid separation is performed, a light phase scrap system is collected in a receiving device, and a heavy phase is directly overflowed to a second-level centrifugal extractor. At the same time, a second-level extractant (isoamyl alcohol) is continuously quantified and delivered to the second-level centrifugal extractor, and similarly a separated scrap light phase enters the receiving device. The heavy phase continuously enters an extraction heavy phase receiving device, and then enters the next operation unit after temporary storage. Herein, the temperature of the extraction and liquid separation stage is controlled at −5~0° C.

In a continuous mixing and press-filtering stage, a mass flow meter and a material delivery pump are used for feedback adjustment, as to continuously quantify and deliver the extraction heavy phase to a jacketed coil reactor, and at the same time, a small amount of methanol is automatically and continuously quantified and delivered as a dilution solvent (the same as a subsequent crystallization solvent) and mixed and diluted with the extraction heavy phase in the coil reactor, and a diluted system directly enters press-filtering devices arranged in parallel, as to filter out a small amount of solid impurities. A clarified system enters the receiving device and then enters the next operation unit. Herein, the temperature in the continuous mixing and filtering stage is controlled at −5~0° C.

In a continuous pH adjustment stage, a press-filtered system is fed back and adjusted by the mass flow meter and the material delivery pump, and continuously quantified and delivered to a tube-type plug flow pH adjustment device. At the same time, the material delivery pump for delivering a pH regulator (acetic acid/methanol) receives the measurement results of a pH value detection device online, and adjusts the feeding amount of the pH adjuster according to this feedback, as to achieve the accurate feeding. The two materials are fully mixed in the pH adjustment device, a pH monitoring point is set again at the pH value detection device, and the pH value detection device has a certain volume buffer capacity, and a qualified acid adjustment system is directly and continuously quantified and enters the next treatment stage. Herein, the temperature in the continuous pH adjustment stage is controlled at −10~−5° C.

In a continuous crystallization stage, before a system to be crystallized enters a crystallization device, the material delivery pump is used to continuously quantify a feed in advance to fill the tube-type plug flow crystallization device with the crystallization solvent. Because the material delivery pump, through a large-flow and high-pressure-resistant oscillating device, continuously delivers energy to the tube-type crystallization device, the solid-liquid mixed two phases after the crystallization may not be blocked in it, and a slurry-like system enters the receiving device for temporary storage at a low temperature. At this time, the system is very stable and is not deteriorated over time. After standing for a period of time, it enters the solid-liquid separation device to obtain a qualified product. Herein, the temperature in the continuous crystallization stage is controlled at −20~−15° C.

The results are shown in Table 1.

Contrast Example 1

A 4 L ertapenem crude product system is post-treated by a batch treatment mode, and the results are shown in Table 1.

volume of 5 L for continuous extraction and separation, and the retention time of the system is only 3~5 min.

In a continuous mixing and press-filtering stage, an extraction heavy phase and a small amount of methanol (the methanol is 60% of the weight of the extraction heavy phase) are continuously mixed in a 3-8 L jacketed coil reactor, the continuous feeding is stable and rapid, and the retention time of the system in the mixing stage is only 3~5 min. Then it enters a second-level parallel filtering device membrane pile for rapid filtering, and the treatment flux of the membrane pile is 1 L~2 L/min, it is matched with the feeding rate of the upstream mixing.

In a continuous pH adjustment stage, the continuous pH adjustment adopts an online pH meter, as to achieve the automatic feedback adjustment, and a 20 L continuous stirring reaction device is adopted, an adjusted qualified system is quickly transferred to a downstream operation through the a 8 L overflow pipeline. While being adjusted, the retention time of the system is only 5~8 min, so the deterioration rate of the product is greatly reduced.

In a continuous crystallization stage, an oscillating flow tube-type crystallization device is used, and the retention volume is 6 L. The system and a crystallization solvent are uniformly mixed in the device for crystallization, the crystal shape of a precipitated crystal is relatively stable, and the retention time of the system is 5~8 min.

The results are shown in Table 2.

Contrast Example 2

A 4 L ertapenem crude product system is post-processed by a batch treatment mode, it is specifically as follows.

In an extraction and liquid separation stage: a 3000 L kettle is used for batch extraction and liquid separation operations, the retention time of the system in this stage is 6.5 h, and the extraction effect is poor.

In a mixing and filtering stage: a batch operation, a 3000 L kettle is used for a mixing operation of system and methanol, the mixing process may have a heat release situation, and the batch operation may have a risk that the local heat release is large so as to damage the product.

In a pH adjustment stage: a batch operation, a 3000 L kettle is used for the operation, a pH of an upstream system is 7.2~9.5, and a methanol/acetic acid system with a pH of

TABLE 1

| Operation mode | Solvent residue in extraction and liquid separation product | | | Product loss in mother liquor after crystallization | Purity | Yield | Retention time of particles in acid adjustment |
| --- | --- | --- | --- | --- | --- | --- | --- |
| | NEP | TMG | Isoamyl alcohol | | | | |
| Embodiment 1 | 0.2% | 0.1% | 0.7% | 12.3% | 96.11% | 54.5% | 3 min |
| Contrast example 1 | 3.45% | 0.3% | 2.26% | 13.3% | 97.75 | 53% | 1.5 h |

Embodiment 2

The 4 L small-scale test in Embodiment 1 is enlarged to a 400 L pilot-scale test. The devices and reagents used are the same as those in Embodiment 1, a difference is as follows:

In a continuous extraction and liquid separation stage: an ertapenem crude product system is continuously fed into a second-level centrifugal extractor with a total retention 3~4 is successively added to the kettle during adjustment, and each time of addition requires stirring, standing, sampling and detecting, until the PH of the system meets the process requirements. At this stage, the product deterioration rate is very fast, so it needs to be performed quickly, and the retention time of the batch operation system is longer, so that the deterioration rate is higher.

In a crystallization stage: a batch operation, it is performed in a 3000 L kettle. During the operation, methanol/n-propanol is added to the kettle for several times in batches.

A purpose of several batches is to gradually induce the precipitation of a crystal nucleus. There are two hidden dangers in this operation, one is that the concentration of a local crystal-forming solvent is too high, and it causes the crystal shape of the precipitated crystal to be unstable. In addition, the products in other areas of the kettle that do not contact with the crystal-forming solvent are still in a state of rapid deterioration. The retention time of the operation system at this stage is also longer, and the product deterioration rate is still higher.

The results are shown in Table 2.

TABLE 2

| Extraction and liquid separation stage | Operation temperature | Operation pressure | Retention time | Extraction effect | | Deterioration rate |
| --- | --- | --- | --- | --- | --- | --- |
| | | | | NEP content | Isoamyl alcohol content | |
| Embodiment 2 | −5~0° C. | Normal pressure | 3~5 min | 0.2% | 0.7% | About 0 |
| Contrast example 2 | −5~0° C. | Normal pressure | 360~400 min | 3.45% | 2.26% | 1.2% |

| Mixing and filtering stage | Operation temperature | Operation pressure | Retention time | System solid content after filtration | Deterioration rate |
| --- | --- | --- | --- | --- | --- |
| Embodiment 2 | −5~0° C. | Normal pressure | 5~8 min | 0 | About 0 |
| Contrast example 2 | −5~0° C. | Normal pressure | 360~400 min | 0 | About 1.2% |

| PH adjustment stage | Operation temperature | Operation pressure | Retention time | pH value | Deterioration rate |
| --- | --- | --- | --- | --- | --- |
| Embodiment 2 | −5~0° C. | Normal pressure | 5~8 min | 6.1-6.3 | 0.5% |
| Contrast example 2 | −5~0° C. | Normal pressure | 200~240 min | 6.1-6.3 | About 4~5% |

| Crystallization stage | Operation temperature | Operation pressure | Retention time | | Deterioration rate |
| --- | --- | --- | --- | --- | --- |
| Embodiment 2 | −20~−15° C. | Normal pressure | 5~8 min | — | 0.1% |
| Contrast example 2 | −20~−15° C. | Normal pressure | 240~300 min | — | About 1~2% |

It is found from the results that: for the 400 L pilot-scale of the ertapenem post-treatment system, the total treatment time of the continuous integrated post-treatment mode is 76.25% shorter than that of the batch post-treatment. The product purity is increased by 4%~6%, and the product yield is increased by about 5%. The occupied area of the device is reduced by 60%, and the operating human resources are reduced by 80%.

It may be seen from the above data:

1. The continuous integrated post-treatment device for the penem product improves a traditional post-treatment mode of the penem product. It is well-known that the penem product system to be treated is very easy to deteriorate. In the case of the ertapenem, the deterioration rate per hour of the system before the pH adjustment is 0.3%, and the deterioration rate per hour after the pH adjustment is 1.2% (this is an inherent loss and may not be changed), and the loss amount may only be reduced by compressing the treatment time.

2. In the traditional batch post-treatment penem product, the loss amount due to the deterioration is 6%~10%. It is mainly because the treatment time of each operation unit is too long. The continuous integrated post-treatment shortens the treatment time of all operation units. Based on the operation time of the extraction and liquid separation before the pH adjustment and mixing and press-filtering, under the same treatment volume of 400 L, the batch treatment requires 12 hours to lose 4% of the product, and the continuous treatment only requires 4 hours to lose 1% of the product.

3. The advantages of the continuous integrated post-treatment device for the penem may be greatly reflected in the pH adjustment stage. In the continuous post-treatment, the retention time of a single particle of the system after the pH is adjusted is 8 min, and the retention time of a single particle of the batch is 4 h. About 5% of the loss is directly reduced.

4. The amount of organic three wastes generated by the post-treatment of the penem product is very large (product system: three wastes=1:5; a volume ratio), the batch treatment may accumulate a large amount of the organic three wastes in a short time, and a potential risk coefficient is high. The continuous integrated post-treatment mode may effectively control the output of the three wastes per unit time and reduce the potential risk coefficient.

The above are only preferred embodiments of the present disclosure, and are not used to limit the present disclosure. For those skilled in the art, the present disclosure may have various modifications and changes. Any modifications, equivalent replacements, improvements and the like made within the spirit and principle of the present disclosure should be included in a scope of protection of the present disclosure.

What is claimed is:

1. A continuous post-treatment method for a penem compound, comprising the following steps:
   S1, performing continuous extraction on a reaction crude product of a penem compound, to obtain an extraction heavy phase and an extraction light phase;
   S2, performing continuous solid-liquid separation on the extraction heavy phase, to obtain a liquid phase separation product;
   S3, performing continuous pH adjustment on the liquid phase separation product until a pH value thereof is 6.1-6.3, to obtain pH-adjusted solution; and
   S4, performing continuous crystallization treatment on the pH-adjusted solution by a first crystallization solvent, then obtain a penem compound product.

2. The method according to claim 1, wherein before performing the continuous solid-liquid separation on the extraction heavy phase, the step S2 further comprises a step of adding a second crystallization solvent to the extraction heavy phase and mixing the two in a plug flow reactor; and the added amount of the second crystallization solvent is 50~80% of the weight of the extraction heavy phase, and the temperature of the plug flow reactor is controlled to −7~3° C.

3. The method according to claim 2, wherein the retention time of the extraction heavy phase in the plug flow reactor is 2~8 min.

4. The method according to claim 1, wherein in the step S1, the continuous extraction process comprises N times in sequence, N≥2, and the heavy phase separated in the M-th time of the continuous extraction process enters the M+1-th time of the continuous extraction process, 1≤M≤(N−1), the heavy phase separated in the N-th time of the continuous extraction process is used as the extraction heavy phase in the step S2.

5. The method according to claim 4, wherein in the continuous extraction process, the retention time of the reaction crude product of the penem compound is 1~7 min, and the treatment temperature is −7~3° C.

6. The method according to claim 1, wherein in the process of the continuous solid-liquid separation, the extraction heavy phase is divided into a plurality of parts, and the plurality of the parts of the extraction heavy phases respectively enter different press-filtering devices for treatment each to each, and the treatment flux of each press-filtering device is 1~2 L/min, the retention time of the extraction heavy phase is 2~11 min.

7. The method according to claim 2, wherein the first crystallization solvent is selected from one or more of a group consisting of methanol and n-propanol, and the second crystallization solvent is selected from one or more of a group consisting of methanol and n-propanol.

8. The method according to claim 1, wherein in the continuous crystallization treatment process, the retention time of the pH-adjusted solution is 2~11 min, and the treatment temperature is −22~12° C.

9. The method according to claim 1, wherein in the step S3, a reagent for adjusting a pH value of a liquid phase separator is a mixed solution of methanol and acetic acid.

10. The method according to claim 9, wherein in the process of adjusting the pH value of the liquid phase separator, the retention time of the liquid phase separator is 2~11 min, and the treatment temperature is −7~3° C.

11. A continuous post-treatment device for a penem compound, comprising:
   a continuous extraction and liquid separation unit (10), provided with a penem compound crude product inlet, an extractant inlet, an extraction heavy phase outlet and an extraction light phase outlet, wherein the continuous extraction and liquid separation unit (10) is used for continuous extraction of a reaction crude product of the penem compound;
   a continuous press-filtering unit (20), provided with a press-filtering inlet, a solid phase outlet and a liquid phase outlet, wherein the press-filtering inlet is connected with the extraction heavy phase outlet, and the continuous press-filtering unit (20) is used for continuous solid-liquid separation of the extraction heavy phase discharged from the extraction heavy phase outlet;
   a continuous pH adjustment unit (30), provided with a liquid phase inlet, a pH adjuster inlet and an adjusting liquid outlet, wherein the liquid phase inlet is connected with the liquid phase outlet, and the continuous pH adjustment unit (30) is used for continuous pH adjustment of the liquid discharged from the liquid phase outlet; and
   a continuous crystallization unit (40), provided with an adjusting liquid inlet, a first crystallization solvent inlet and a crystallization slurry outlet, wherein the adjusting liquid inlet is connected with the adjusting liquid outlet, and the continuous crystallization unit (40) is used for continuous crystallization of the pH-adjusted solution discharged from the adjusting liquid outlet.

12. The device according to claim 11, wherein the device further comprises:
   a plug flow reactor (50), arranged on a pipeline connected with the press-filtering liquid inlet and the extraction heavy phase outlet, and the plug flow reactor (50) is further provided with a second crystallization solvent inlet.

13. The device according to claim 12, wherein the plug flow reactor (50) is a jacketed coil reactor, and it comprises a coil reactor and a first temperature control jacket arranged outside the coil reactor.

14. The device according to claim 11, wherein the continuous pH adjustment unit (30) is a tube-type pH adjustment device and the continuous crystallization unit (40) is a tube-type crystallization device.

15. The device according to claim 12, wherein the device further comprises: a pH value detection device (60), arranged on a pipeline connected with the adjusting liquid inlet and the adjusting liquid outlet, and used to detect a pH value of the pH-adjusted solution.

16. The device according to claim 11, wherein the continuous extraction and liquid separation unit (10) comprises multi-level of continuous extraction and liquid separation devices (11) arranged serially in sequence, and each continuous extraction and liquid separation device (11) is provided with a liquid inlet, an extractant inlet, an extraction light phase outlet and an extraction heavy phase outlet, and the liquid inlet of the continuous extraction and liquid separation device (11) located at the most upstream is the penem compound crude product inlet, and the extraction heavy phase outlet of the continuous extraction and liquid separation device (11) located at the most downstream is connected with the press-filtering liquid inlet, and in two adjacent continuous extraction and liquid separation devices (11), the extraction heavy phase outlet located in the upstream level is connected with the liquid inlet located in the downstream level.

17. The device according to claim 11, wherein the continuous press-filtering unit (20) comprises multi-level press-filtering devices (21) arranged in parallel, and each multi-level press-filtering device (21) is provided with a press-filtering inlet, a solid phase outlet and a liquid phase outlet.

18. The device according to claim 15, wherein the device further comprises:
- an extraction light phase receiving device (70), connected with the extraction light phase outlet;
- an extraction heavy phase receiving device (80), arranged on a pipeline connected with the extraction heavy phase outlet and the plug flow reactor (50);
- a liquid phase receiving device (90), arranged on a pipeline connected with the liquid phase inlet and the liquid phase outlet; and
- a crystallization slurry receiving device (100), connected with the crystallization slurry outlet.

19. The device according to claim 18, wherein the device further comprises:
- a first mass flow meter (110), arranged on a pipeline connected with the extraction heavy phase receiving device (80) and the plug flow reactor (50);
- a second mass flow meter (120), arranged on a pipeline connected with the liquid phase receiving device (90) and the liquid phase inlet; and
- the device further comprises a control unit, wherein the control unit is electrically connected with the pH value detection device (60), the first mass flow meter (110) and the second mass flow meter (120).

20. The device according to claim 12, wherein the pipelines on which the penem compound crude product inlet, the extractant inlet, the pH adjuster inlet, the liquid phase inlet, the first crystallization solvent inlet, the adjusting liquid inlet, the second crystallization solvent inlet and the inlet of the plug flow reactor (50) for feeding the extraction heavy phase are located are all provided with a material delivery pump (130); wherein, the continuous extraction and liquid separation unit (10), the continuous press-filtering unit (20), the continuous pH adjustment unit (30) and the continuous crystallization unit (40) are all provided with a temperature control unit, and the extraction heavy phase receiving device (80) is provided with a second temperature control jacket, the liquid phase receiving device (90) is provided with a third temperature control jacket, the crystallization slurry receiving device (100) is provided with a fourth temperature control jacket, and the control unit is also electrically connected with the temperature control unit, the second temperature control jacket, the third temperature control jacket and the fourth temperature control jacket.

* * * * *